United States Patent [19]

Atsuta et al.

[11] Patent Number: 4,966,766
[45] Date of Patent: Oct. 30, 1990

[54] CURABLE COMPOSITIONS FOR DENTAL DRUGS HAVING SUSTAINED RELEASE PROPERTY

[75] Inventors: Mitsuru Atsuta, Nagasaki; Takeshi Sakashita, Yamaguchi; Ryoichi Miyamoto, Kyoto; Yukinori Tanimura, Yamaguchi; Saburo Fuji, Hiroshima, all of Japan

[73] Assignee: Mitsui Petrochemical Industries, Ltd., Tokyo, Japan

[21] Appl. No.: 478,361

[22] Filed: Feb. 12, 1990

Related U.S. Application Data

[60] Division of Ser. No. 189,528, Apr. 7, 1988, Pat. No. 4,925,660, which is a continuation-in-part of Ser. No. 933,241, Nov. 21, 1986, abandoned.

[30] Foreign Application Priority Data

| | | |
|---|---|---|
| Nov. 21, 1985 [JP] | Japan | 60-259900 |
| Jul. 18, 1986 [JP] | Japan | 61-168096 |
| Nov. 4, 1986 [JP] | Japan | 61-260766 |

[51] Int. Cl.$^5$ ............................................. A61F 13/00
[52] U.S. Cl. .................................... 424/422; 424/81
[58] Field of Search ................................. 424/422, 81

[56] References Cited

U.S. PATENT DOCUMENTS

| | | | |
|---|---|---|---|
| 4,302,381 | 11/1981 | Omura et al. | 526/323.1 |
| 4,310,397 | 1/1982 | Kaetsu et al. | 424/81 |

FOREIGN PATENT DOCUMENTS

| | | |
|---|---|---|
| 0020777 | 7/1981 | European Pat. Off. . |
| 0140766 | 8/1985 | European Pat. Off. . |
| 2511122 | 9/1976 | Fed. Rep. of Germany . |
| 2226140 | 4/1974 | France . |
| 2226160 | 11/1974 | France . |

OTHER PUBLICATIONS

Organic Chemistry Textbook for Fieser and Fieser, 1956, pp. 821–822, "Flavones".

M. Addy et al; "The Effects of the Incorporation of Chlohexidine Acetate on Some Physical Properties of the Polymerized and Plasticized Acrylics"; pp. 155–163; vol. 8; 1981.

*Primary Examiner*—Joseph L. Schofer
*Assistant Examiner*—N. Sarofim
*Attorney, Agent, or Firm*—Burns, Doane, Swecker & Mathis

[57] ABSTRACT

A crude drug ingredient having bactericidal activity incorporated into a curable composition comprising a (meth)acrylate type monomer, a polymerization initiator and if necessary a filler to formulate the ingredient into the drug having sustained release property. The curable composition containing the crude drug ingredient is applied to a defective part of a tooth or an artificial gum for preventing dental diseases such as carious tooth, pyorrhea alveolaris, and the like.

3 Claims, No Drawings

CURABLE COMPOSITIONS FOR DENTAL DRUGS HAVING SUSTAINED RELEASE PROPERTY

This application is a divisional of application Ser. No. 189,528, filed Apr. 7, 1988, now U.S. Pat. No. 4,925,660, which is a continuation-in-part of application Ser. No. 933,241 filed Nov. 21, 1986 (now abandoned).

BACKGROUND OF THE INVENTION

This invention relates to curable compositions for drugs having sustained release property, and more particularly to curable compositions for dental drugs having sustained release property, cured polymerizates thereof and methods for preventing dental diseases wherein active ingredients of said drugs are gradually released in the mouth over a long period of time, thereby preventing dental diseases such as carious tooth, pyorrhea alveolaris, etc.

Carious tooth which is most frequently observed in dental diseases is caused by various oral microorganisms (Streptococcus mutans is well known out of these micro-organisms) present in the mouth. On one hand, such dental diseases as pyorrhea alveolaris and others are induced by the bacteria contained in dental plaque. Accordingly, an effective means to prevent such dental diseases as carious tooth, pyorrhea alveolaris, etc. is to inhibit propagation of bacteria in the mouth as well as formation of dental plaque.

Under the circumstances, we have studied various drugs from the standpoint of preventive dentistry, and eventually have come to the conclusion that in order to inhibit the propagation of bacteria in the mouth as well as the formation of dental plaque, the use of crude drug ingredients having bactericidal activities is effective for the purpose intended since they bring about less side-effects even when administered for an extended period of time, assuring safety in application and mild activities. However, a mere application of such crude drug ingredients directly to intra-oral sites results in unsustained pharmacological effect of said crude drug ingredients, and thus no desired effect can be achieved.

Now, we have made further study in view of the above, and found that if crude drug ingredients having bactericidal activities are applied to intra-oral sites in the sustained release form, the bactericidal ingredients are gradually released to effectively inhibit the formation of dental plaque and the propagation of bacteria in the mouth over a long period of time, and hence it is advantageous to formulate the crude drug ingredients into the preparations having sustained release property wherein said ingredients are incorporated in a suitable matrix.

Preparation of drugs having sustained release property by including active ingredients of the drugs in a polymer matrix is disclosed in Japanese Patent Laid-Open-to-Public No. 62012/1980 and Japanese Patent Publn. No. 17001/1982. The drugs disclosed in these publications, however, are all directed to the treatment of internal diseases occurring in digestive canals, systems of circulation, etc. and are applied to in oral dosage forms or applied to mucous membrane in the mouth and are not intended to the prevention of dental diseases such as carious tooth, pyorrhea alveolaris, etc. So far as we are aware of, it is not known that crude drug ingredients are formulated into drugs having sustained release property for the purpose of preventing dental disease.

An object of the invention is to provide curable compositions for preparing drugs having sustained release property which are highly effective in preventing such dental diseases as carious tooth, pyorrhea alveolaris, etc. in a simple and practically easy manner.

These and other objects of the invention will be apparent from the following detailed description thereof.

DESCRIPTION OF THE INVENTION

The curable compositions for drugs having sustained release property comprise a (meth)acrylate type monomer, a polymerization initiator, a crude drug ingredient having bactericidal activity and, if necessary, a filler. The compositions as applied finally, for example, to a cavity of decayed tooth, are found to be excellent in mechanical strength such as abrasion resistance, hardness and compression strength since the applied composition is polymerized by application thereto of light or heat or polymerized at ordinary temperatures with a redox initiator to form a cured product in said cavity. Furthermore, the present curable compositions are applied to hard resins for artificial teeth, resins for tooth bed, fillers for carious tooth and the like, by mixing a bactericidal crude drug ingredient with (meth)acrylate in its monomer state prior to the polymerization thereof and hence said ingredient can be uniformly dispersed in the curable compositions.

The curable compositions of the present invention comprise a (meth)acrylate monomer (hereinafter called component (a)), a polymerization initiator (hereinafter called component (b)) and a crude drug having bactericidal property (hereinafter called component (c)), or comprise a filler (hereinafter called component (d)) in addition to the above-mentioned components.

The component (a) includes acrylate monomers having one or more acryloyloxy groups per one molecule, or methacrylate monomers having one or more methacryloyloxy groups per one molecule. In the present invention, for convenience's sake these monomers are generically called "(meth)acrylate type monomers".

Not limitative but illustrative examples of the (meth)acrylate type monomers include alkyl (meth)acrylates such as methyl acrylate, ethyl acrylate, methyl methacrylate, ethyl methacrylate, butyl methacrylate, etc., 2-hydroxyethyl acrylate, 2-hydroxyethyl methacrylate, ethylene glycol di(meth)acrylate, propylene glycol di(meth)acrylate, triethylene glycol di(meth)acrylate, tripropylene glycol di(meth)acrylate, neopentyl glycol di(meth)acrylate, butylene glycol di(meth)acrylate, hexylene glycol di(meth)acrylate, 2,2-bis[4-(meth)acryloyloxyphenyl]propane, 2,2-bis[4-(meth)acryloyloxycyclohexyl]propane, 2,2-bis[3-(meth)acryloyloxy-2-hydroxypropoxyphenyl]propane, 2,2-bis[2-(meth)acryloyloxyethoxyphenyl]propane, 1,3-bis[(meth)acryloyloxyethoxy]benzene, 2,2-bis[2-(meth)acryloyloxydiethoxyphenyl]propane, 1,4-bis[(meth)acryloyloxyethoxy]benzene, trimethylolpropane tri(meth)acrylate, pentaerythritol tetra(meth)acrylate, dipentaerythritol hexa(meth)acrylate, γ-methacryloxypropyl trimethoxysilane, γ-methacryloxypropyl tri(trimethylsiloxy)silane, γ-methacryloxypropyl pentamethyldisiloxane, di(methacryloxyethyl)trimethyl hexamethylenediurethane,

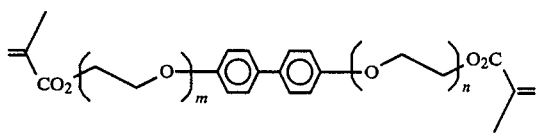

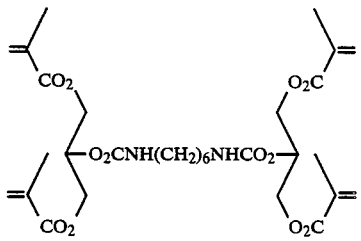

Of these monomers as recited above, (meth)acrylate type monomers having two or more (meth)acryloyloxy groups per one molecule are preferred, since they can provide easy control of sustained release property and high strength of the resulting compositions.

The component (b) which can be used in the present invention includes physiologically acceptable substances selected from those which readily decompose by application of heat or light to form radicals, i.e. commonly used thermal polymerization initiators or photopolymerization initiators.

Exemplified as useful thermal polymerization initiators are organic peroxides such as diacetyl peroxide, dipropyl peroxide, dibutyl peroxide, dicapryl peroxide, dilauryloyl peroxide, dibenzoyl peroxide, p,p'-dichlorobenzoyl peroxide, p,p'-dimethoxybenzoyl peroxide, p,p'-dimethylbenzoyl peroxide, p,p'-dinitrobenzoyl peroxide, etc. Among these dialkyl peroxides is preferred dibenzoyl peroxide.

Photopolymerization initiators include α-ketocarbonyl compounds, for example, α-diketones, α-ketoaldehydes, α-ketocarboxylic acids, α-ketocarboxylic acid esters, etc. More particularly, exemplified are α-diketones such as diacetyl, 2,3-pentadione, 2,3-hexadione, benzyl, 4,4'-dimethoxybenzyl, 4,4'-diethoxybenzyl, 4,4'-oxybenzyl, 4,4'-dichlorobenzyl, 4-nitrobenzyl, α-naphthyl, β-naphthyl, camphorquinone, 1,2-cyclohexanedione, etc.; α-ketoaldehydes such as methylglyoxal, phenylglyoxal, etc.; pyruvic acid, benzoylformic acid, phenylpyruvic acid, methyl pyruvate, ethyl benzoylformate, methyl phenyl-pyruvate, butyl phenylpyruvate, etc. Of the α-ketocarbonyl compounds, it is preferable to use α-diketones from the standpoint of stability or the like.

Furthermore, in the case where either a thermal polymerization initiator or a photopolymerization initiator is used as the component (b), the use in combination therewith of such amines as will be mentioned later is preferable since the polymerization is so accelerated that it can be carried out at ordinary temperatures, and that a cured product high in strength can be obtained thereby.

Such amines may be any of aliphatic, alycyclic and aromatic amines, and they may be of primary, secondary and tertiary amines, but aromatic amines are preferred with especially preferable tertiary amines.

Typical examples of such useful amines include aliphatic amines such as triethylamine, tripropylamine, tributylamine, tripentylamine, trihexylamine, trioctylamine, diethylamine, dipropylamine, dibutylamine, dihexylamine, butylamine, hexylamine, octylamine, decylamine, dodecylamine, N,N-dimethylaminoethyl methacrylate, N,N-diethylaminoethyl methacrylate and the like; alicyclic amines such as tricyclohexylamine, dicyclohexylamine, cyclohexylamine and the like; and aromatic amines such as aniline, toluidine, xylidine, phenylenediamine, N,N-dimethylaniline, N,N-diethylaniline, N,N-di(β-hydroxyethyl)aniline, N,N-dimethyltoluidine, N,N-diethyltoluidine, N,N-dimethylanisidine, N,N-diethylanisidine, N,N-dimethyl-t-butylaniline, N,N-diethyl-t-butylaniline, N,N-dimethyl-p-chloroaniline, diphenylamine, N,N-bis(β-hydroxyethyl)-p-toluidine, 4-dimethylaminobenzoic acid, methyl 4-dimethylaminobenzoate, 4-dimethylaminobenzaldehyde, 4-diethylaminobenzoic acid, methyl 4-diethylaminobenzoate, N,N-dimethyl-p-cyanoaniline, N,N-dimethyl-p-bromoaniline and the like.

The amount of the component (b) used, based on 100 parts by weight of the component (a), is usually in the range of from 0.01 to 15 parts by weight, preferably from 0.03 to 10 parts by weight, and more preferably from 0.05 to 5 parts by weight. The amount of the amine used in combination with the component (b) is usually in the range of from 0.01 to 15 parts by weight based on 100 parts by weight of the component (a).

The component (c) is a crude drug ingredient having bactericidal activities effective in inhibiting formation of dental plaque and propagation of oral microorganisms in the mouth. So far as we are aware of, there is no case where this component (c) was used as medicinal ingredient having sustained release property. Since such a crude drug ingredient as the component (c) used in the present invention has a mild activity and does not show undesired side-effects even when used for a long period of time, it exhibits lasting effects on the prevention of dental diseases such as carious tooth (saprodentia), pyorrhea alveolaris and the like.

Useful as the crude drug ingredients are such substances as flavonoids, benzenecarboxylic acids, benzopyrones, steroids and terpenes. Of these substances, however, the following substances are preferably used when their compatibility with the component (a) is taken into account. Preferable are anethole, anisaldehyde, anisic acid, cinnamic acid, asarone, furfuryl alcohol, furfural, cholic acid, oleanolic acid, ursolic acid, sitosterol, cineol, curcumine, alanine, arginine, homocerine, mannitol, berterine, bergapten, santonin, caryophyllene, caryophyllene oxide, terpinene, chymol, terpinol, carvacrol, carvone, sabinene, inulin, lawsone, hesperedin, naringenin, flavone, flavonol, quercetin, apigenin, formonoretin, coumarin, acetyl coumarin, magnolol, honokiol, cappilarin and aloetin. Although it is required that said crude drug ingredients have some extent of mechanical strength, hesperedin, naringenin and quercetin among flavonoids, anisic acid among benzene carboxylic acids, acetyl coumarin among benzopyrones, sitosterol among steroids, and caryophyllene and caryophyllene oxide among terpenes are especially preferable since no decrease in mechanical strength of the resulting composition is observed even when these substances are incorporated into said composition.

The amount of the component (c) to be incorporated, based on 100 parts by weight of the component (a), is usually in the range of from 0.01 to 50 parts by weight, preferably from 0.05 to 40 parts by weight, and especially preferably 1 to 30 parts by weight, though said amount should be decided depending on the degree of bactericidal activity of each crude drug ingredient used from the standpoint how long the preventive effects of dental diseases such as carious tooth (saprodentia), pyorrhea alveolaris or the like are intended to continue.

The filler as the component (d) is desirably incorporated into the curable compositions of the present invention since the incorporation thereof makes it possible to increase the cured polymers resulted therefrom in mechanical strength such as abrasion resistance, hardness, compression strength, etc., and to control release of the crude drug ingredient from the cured polymers to a certain extent. Usable as the fillers of the type are physiologically acceptable inorganic and organic fillers.

Usable as the inorganic fillers are glass powder (including barium glass powder), silica of 1-10 microns in particle diameter, fused silica, ultrafine silica (including those of 1-1000 millimicrons in particle diameter), alumina, silica alumina, zirconia, zeolite, etc. On one hand, useful organic fillers include, for example, such organic composite fillers as prepared by coating the particle surface of glass powder, glass bead-like silica, fused silica or ultrafine silica with methacrylate type polymers.

Of the fillers mentioned above, preferable are such porous substances as silica, alumina, silica alumina, and zeolite since they inherently possess adsorptivity and not only temporarily adsorb the crude drug ingredient but also gradually release the same with the lapse of time, thereby further improving sustained release property of the crude drug ingredient incorporated. Though a particle size of the filler is not a decisive factor, it is preferable that the particle is in the range of from about 0.01 micron to 100 microns from the standpoint of easiness in handling.

The amount of the filler used, based on 100 parts by weight of the component (a), is usually in the range of from 1 to 1000 parts by weight, preferably from 10 to 1000 parts by weight, and especially preferably from 80 to 900 parts by weight.

In addition to the above-mentioned components, the present curable compositions can be incorporated with various additives such as colorants, polymerization regulators, etc.

Where the curable compositions of the present invention comprising the above-mentioned components are applied to the preventive treatment of dental diseases such as carious tooth, pyorrhea alveolaris, etc., an affected part, for example, a cavity of the tooth, is filled with said composition which is usually in a paste-like state, and thereafter the (meth)acrylate type monomer of the component (a) in the filled composition is polymerized using a redox initiator or with a light radiation to provide a cured product in the cavity. In that case, when a thermal polymerization initiator is used as an initiator for the polymerization of the curable composition, it is preferably used in combination with the above recited amines. The curing temperature is usually from 0° to 50° C., preferably from 5° to 40° C., and the time required for curing the composition is usually from 0.5 to 20 minutes, preferably from 1 to 10 minutes. When a photopolymerization initiator is used as a polymerization initiators for the curable composition, the composition usually cures by the irradiation with light rays for 1 second to 5 minutes. The light rays used may be either natural or artificial light rays ranging from ultraviolet region to visible light range. As a source of the artificial light rays, there may be used high pressure mercury lamp, medium pressure mercury lamp, low pressure mercury lamp, halogen lamp, tungsten lamp, etc. The temperature employed at the time of irradiation of light rays is in the range of from 0° to 50° C., preferably from 5° to 40° C.

Since a cured polymerizate is the final form, when applied to tooth, of the curable composition having sustained release property, into which a crude drug ingredient has been incorporated, said cured polymerizate is firmly fixed to the position of the tooth to which the cured polymerizate has been applied, and does not decrease in mechanical strength even when exposed for a long period of time to a wet environment in the mouth, and consequently the cured polymerizate does not fall off even when applied to any position in the mouth where momentum is large, and thus the preventive effect higher by far than that of the prior art compositions is expected. Furthermore, the curable compositions of the present invention can also be extensively used not only for the prevention of dental diseases but also as dental materials for filling and reparing purposes. As an example of the alternative uses referred to above, there may be mentioned composite resins, hard resins, resins for tooth bed, sealants or artificial teeth.

Because of containing crude drug ingredients having bactericidal activities, the curable compositions of the present invention possess such an advantage that bectericidal performances that cannot be observed in the prior art dental materials are exhibited even when they are used for the above-mentioned alternative purposes.

The present invention is illustrated below in more detail with reference to examples, but it should be construed that the invention is in no way limited to those examples only.

EXAMPLE 1

A mixture comprising 50 parts by weight of trimethylolpropane trimethacrylate, 50 parts by weight of 2,2,4-trimethylhexamethylene diisocyanate/hydroxyethyl methacrylate=$\frac{1}{2}$ (mol/mol) adduct (hereinafter called "UDMA" for short), 60 parts by weight of Aerosil ® (Aerosil OX 50 produced and sold by Nippon Aerosil Co., Ltd.) and 1 part by weight of benzoyl peroxide was kneaded with a roll. Thereafter, the kneaded mixture was heated for 10 minutes at a pressure of 100 kg/cm² and a temperature of 120° C. by means of a press to form it into a plate-like product which was then ground with a ball mill to obtain a particulate organic composite filler of about 10 micron in particle diameter.

A paste-like product was obtained by mixing together 225 parts by weight of this organic composite filler obtained above, 100 parts by weight of UDMA, 0.06 part by weight of camphorquinone and 10 parts by weight of quercetin. This paste-like product was irradiated for 90 seconds with light from a xenon lamp for dental surgery (DENTACOLAR manufactured and sold by Kulzer, West Germany) to obtain a cured product. The cured product was found favorable, having Brinell hardness of 22, compression strength of 2800 kg/cm², and bending strength of 630 kg/cm².

One (1) gram of this cured product (4 test specimens of 10 mm φX 2,3 mm, the weight was adjusted by thickness) was immersed in 1 ml of water and then extracted with distilled water at a rate of the amount of water supplied=the amount of water drained=1 liter/day, and after concentrating the drained water to 25 ml, the amount of quercetin present in the drain water was measured by using UV spectrum to obtain the results as shown in Table 1.

TABLE 1

| | Amount of quercetin eluted (1.0 g of the test specimen used) | | | | |
|---|---|---|---|---|---|
| | After one day | After 2 days | After 6 days | After 10 days | After 30 days |
| Amount eluted (microgram) | 42 | 2.5 | 2.2 | 2.2 | 0.9 |

EXAMPLE 2

A cured product was prepared in a similar manner to that of Example 1 but using 10 parts by weight of hesperedin in place of 10 parts by weight of quercetin used therein.

The cured product had Brinell hardness of 23, compression strength of 2730 kg/cm$^2$ and bending strength of 680 kg/cm$^2$.

This cured product was immersed in 1 ml of water, and was extracted with water in the same manner as in Example 1 to measure the amount of hesperetin present in the extract by means of UV spectrum. The results are as shown in Table 2.

TABLE 2

| | Amount of hesperedin eluted (1.0 g of the test specimen used) | | | | |
|---|---|---|---|---|---|
| | After one day | After 2 days | After 6 days | After 10 days | After 30 days |
| Amount eluted (microgram) | 45 | 2.8 | 2.0 | 1.9 | 0.6 |

EXAMPLE 3

A paste-like product was obtained from a mixture comprising 155 parts by weight of the same organic composite filler as obtained in Example 1, 115 parts by weight of Aerosil (Aerosil RM 50 produced and sold by Nippon Aerosil Col., Ltd. - the fillers totalling to 270 parts by weight of triethylene glycol dimethacrylate, 50 parts by weight of UDMA, 25 parts by weight of 1,3-bis(methacryloxyethoxy)benzene, (poly(meth)-acrylic acid ester monomers totalling to 100 parts by weight), 0.15 part by weight of camphorquinone, 0.15 part by weight of 4-diethylaminobenzoic acid and 11 parts by weight of caryophyllene oxide.

This paste-like product was irradiated with light for 40 seconds using a photopolymerization vessel for dental use (TRANSLUX manufactured and sold by Kulzer, West Germany) to obtain a cured product. This cured product had Brinell hadness of 40, compression strength of 3300 kg/cm$^2$ and bending strength of 820 kg/cm$^2$.

This cured product was immersed in 1 ml of water, and was extracted with water in the same manner as in Example 2 to measure the amount of caryophyllene oxide present in the extract by means of UV spectrum. The results are as shown in Table 3.

TABLE 3

| | Amount of caryophyllene oxide eluted (1.0 g of the test specimen used) | | | |
|---|---|---|---|---|
| | After one day | After 2 days | After 6 days | After 10 days |
| Amount eluted (microgram) | 60 | 25 | 10 | 5 |

What is claimed is:

1. A method for preventing or treating dental diseases said method comprising administering to a tooth or an artificial gum of a mammalian organism in need of such treatment an effective amount of a curable composition having a sustained release property which comprises
    (a) a (meth)acrylate type monomer,
    (b) a polymerization initiator, and
    (c) a crude drug ingredient having bactericidal activity.

2. The method of claim 1 wherein said dental disease is carious tooth or pyorrhea alveolaris.

3. The method of claim 1 wherein the curable composition further comprises a filler.

* * * * *